(12) United States Patent
Cho

(10) Patent No.: US 6,866,314 B2
(45) Date of Patent: Mar. 15, 2005

(54) PADDED TWEEZERS

(76) Inventor: Yong Hoon Cho, 604 Murfield Ct., Fullerton, CA (US) 92835

( * ) Notice: Subject to any disclaimer, the term of this patent is extended or adjusted under 35 U.S.C. 154(b) by 38 days.

(21) Appl. No.: 10/407,974

(22) Filed: Apr. 4, 2003

(65) Prior Publication Data
US 2004/0145201 A1 Jul. 29, 2004

Related U.S. Application Data

(63) Continuation-in-part of application No. 10/351,165, filed on Jan. 24, 2003, now abandoned.

(51) Int. Cl.$^7$ ................................................ B25B 9/02
(52) U.S. Cl. .................................. 294/99.2; 294/25
(58) Field of Search ........................... 294/1.1, 8.5, 11, 294/16, 25, 33, 50.8, 99.2; 606/205, 210; 16/422, 430

(56) References Cited

U.S. PATENT DOCUMENTS

| | | | | |
|---|---|---|---|---|
| 1,411,316 A | * | 4/1922 | Vestal | 294/50.8 |
| 2,833,239 A | * | 5/1958 | Larsen | 228/57 |
| 3,280,665 A | * | 10/1966 | Block | 294/99.2 |
| 3,735,426 A | * | 5/1973 | Horvath | 623/65 |
| 3,818,784 A | * | 6/1974 | McClure | 294/99.2 |
| 4,261,608 A | * | 4/1981 | Bradshaw | 294/25 |
| 4,318,313 A | * | 3/1982 | Tartaglia | 294/99.2 |
| 5,190,335 A | * | 3/1993 | Rommerdale | 294/99.2 |
| 5,334,215 A | * | 8/1994 | Chen | 606/210 |
| 6,129,398 A | * | 10/2000 | Calhoun | 294/99.2 |

* cited by examiner

Primary Examiner—Dean J. Kramer
(74) Attorney, Agent, or Firm—Maria Erlinda Co Sarno

(57) ABSTRACT

A tweezers with a touching pad having a soft and resilient pad on each pincer to provide comfort as well as prevent corns and callouses from forming on the fingers. The touching pad is a pad by itself or a pad supported by a pad holder. The pad may be installed directly to the pincers by squeezing the tail portion of the pad into an opening bored on the pincers. The pad may also be supported by a touching pad holder inserted into each pincer of the tweezers. The pad holder generally have an upper or top band bordering an open space joined to either a lower band or an L-shaped claw. The touching pad holder is held to the pincers by inserting a tail portion of the pad into an opening bored on the pincers through the open space bordered by the upper or top band. The touching pad can also be installed on the pincers by sliding a touching pad holder having a planar pad into each pincers. The touching pad is either stationary or movable.

21 Claims, 4 Drawing Sheets

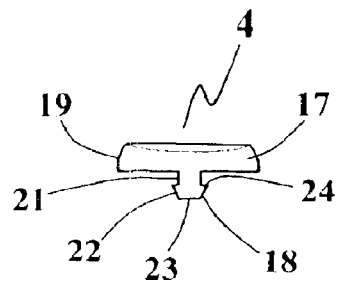
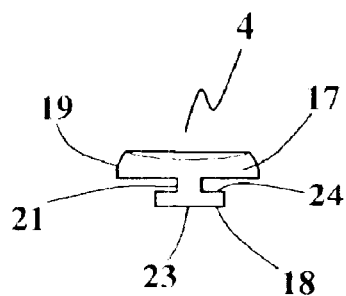
*Fig. 11A*  *Fig. 11B*
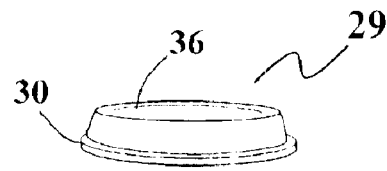
*Fig. 12*
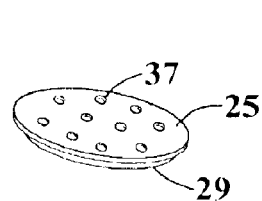
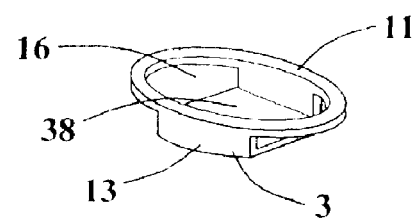
*Fig. 13*  *Fig. 14A*
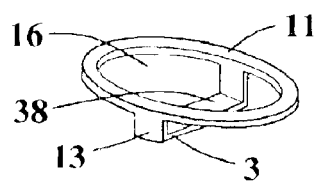
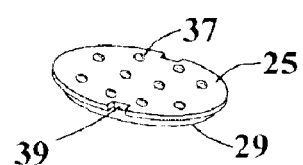
*Fig. 14B*  *Fig. 15*

US 6,866,314 B2

PADDED TWEEZERS

This application is a continuation-in-part of application Ser. No. 10/351,165 filed Jan. 24, 2003 now abandoned.

BACKGROUND

This invention relates to a tweezers having a finger touching pad for better grip and comfortable handling.

Current tweezers in the market are made of metal which press upon the fingers. For persons who constantly and repeatedly use tweezers as part of their job, such as beauticians or seamstresses, the constant pressure from the handling of the tweezers can eventually cause formation of callouses and corns on the affected areas of the fingers. If the use of the tweezers demand precision such as in the microbiology, medical and electronic fields, the smooth metallic surface can cause unwanted slippage or drifting of the fingers that can damage or ruin the desired result in addition to the eventual formation of callouses mentioned above. Sweat, moisture, lotion or moisturizers on the fingers aggravates the situation.

U.S. Pat. No. 5,190,335 is directed towards a control enhancing tweezers. While this device may have enhanced the control of the tweezers, the tweezers arm engaging members which incorporates a finger/thumb receiving and holding platform at its respective tips, surrounds almost three quarters of the body of the tweezers except the moving arms which consequently offer resistance when the moving arms are pinched for closure. The device is specially designed for individuals with reduced or impaired manual dexterity where some resistance to the free movement of the tweezers arms or pincers are desired as well as having more surface area around the body of the tweezers to grab on. If the moving arm is easily moved, one with impaired dexterity will have difficulty at targeting the object desired for picking or plucking. The tweezers also requires more material and more complex molding because the tweezers engaging members must snugly envelope around the body of the tweezers. Further, since the tweezers engaging member extends to the finger/thumb receiving and holding platform as a single piece, the platform is necessarily made of the same material as the engaging members. Because the tweezers engaging members need to be rigid to support the body of the tweezers, the finger/thumb receiving and holding platforms are consequently, also rigid in structure. To provide the grip, the surface of the platform is concave in shape to receive the respective finger. Although this has a concave surface, because it is rigid, the repeated use of this tweezers pose the same problem as the current tweezers in that callouses and corns can potentially form upon repeated usage because the surface that the fingers press on is rigid and hard and the rim protruding around the periphery of the receiving platform accentuates the pressure exerted on the fingers.

It is the object of this invention to provide a tweezers with soft padded surfaces to provide comfortable handling and prevent the formation of corns and callouses on the fingers.

It is also an object of this invention to provide a pad of such materials that will enhance the grip on the device.

It is a further object of the invention to provide a tweezers with a touching pad that does not envelope the body of the tweezers thereby not affecting the free movement of the pincers.

It is still a further object of the invention to provide a padded tweezers that is easy to manufacture.

It is also a further object of the invention to provide a tweezers with a movable touching pad to enable a user to place the pad at a preferred location.

BRIEF DESCRIPTION OF THE DRAWING

FIG. 11A is a front view of a pad having a tapered tail.

FIG. 11B is a front view of a pad having a rectangularly shaped tail.

FIG. 12 is a perspective view of a pad having a planar body without a tail.

FIG. 13 is a plan view of the bottom surface of the pad of FIG. 12 provided with bumps.

FIG. 14A is a perspective view of the touching pad holder having an upper band and a solid wide lower band.

FIG. 14B is a perspective view of the touching pad holder having an upper band and a solid narrow lower band.

FIG. 15 is a plan view of the bottom surface of the pad having a cut out portion on the bottom surface to accommodate the strip joining the solid lower band to the upper band of the pad holder.

SUMMARY OF THE INVENTION

Figure 1:
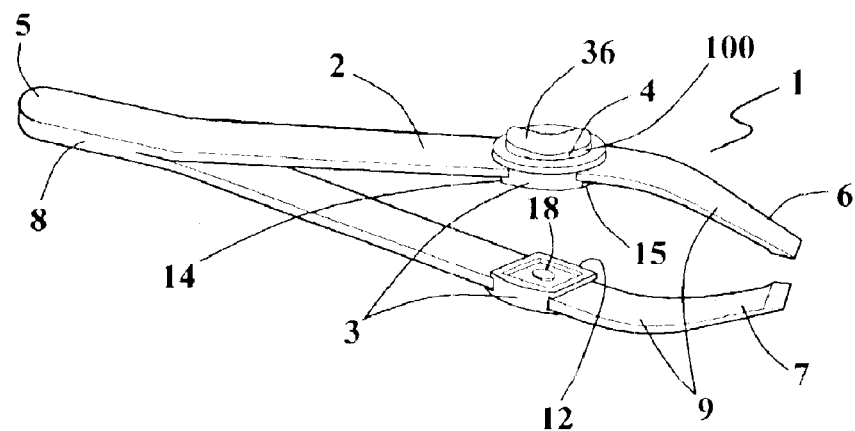
FIG. 1 is a perspective view of a padded tweezers having a pad holder with an upper and a lower band bordering an open space.

This invention relates to a tweezers with finger touching pads on each pincer to improve the grip and prevent formation of callouses and corns. The tweezers comprise of a body having two pincers with a stationary end and a moving end and a touching pad with a soft and resilient pad for each pincer. The touching pad may be a pad by itself or preferably a pad supported by a pad holder. The touching pad can be installed directly into the pincers by one end of the pad snugly plugging into an opening, a hole or track bored on the moving end of the pincer or through a touching pad holder supporting the pad inserted into the pincers. If supported by a touching pad holder, the pad holder is introduced into each pincer at a location or locations on the moving end of the tweezers. Herein, touching pad holder and pad holder are used interchangeably. This location is the position on the pincers that a user usually squeeze on to close the tweezers.

The pad holder comprises an upper or top band having a peripheral contour bordering an open space and a means for keeping the pad engaged with the moving end of the pincers, the means joined at each lateral end of the upper or top band with a strip having a height corresponding to the thickness of the pincers. The means for keeping the pad engaged with the moving end of the pincers may be a lower band having a peripheral contour bordering an open space or it may simply be a solid lower band midpoint of the upper or top band extending across the strip joining the upper or top band. The lower band may or may not be shaped similarly as the upper or top band. Both types of band means, after being joined or connected to the upper or top band by the strip, form a slit beneath the upper or top band through which the pincer is introduced. It is not necessary to form a full slit. The upper or top band may have the joining strip or its two lateral side ends extending downward forming an overhang, each overhang having a tip extending inward to form an L-shaped claw through which the pincer is introduced. The L-shaped claw can also be formed from the lower band bordering an open space by simply cutting off a central portion of the band running across the lateral side ends. The two lateral side ends of the L-shaped claw or the strip joining the upper or top band with the lower band have an outside lateral surface corresponding to the shape of the upper or top band and an inside lateral surface conforming to the outside lateral contour of the pincers. The width of the slit or the opening bordered by the L-shaped claws facing each other and the height of the slit or the L-shaped claw conform to the width and height or thickness of the pincers, respectively, at the point where the touching pad holder sits stationarily on the pincers. For the tweezers having an opening, a hole or track on the pincers to hold the touching pad, the pad has a head portion, a tail portion and a stem connecting the head portion with the tail portion. Here, if the pad is supported by a pad holder, the head portion especially the top surface matches the inside peripheral contour of the upper or top band of the touching pad holder to fill the open space bordered by the upper or top band of the touching pad holder. With or without the pad holder, the head portion preferably has an ergonomically shaped top surface to provide comfort for the fingers. The stem of the pad has a size and shape matching the opening and a height matching the thickness of the pincers to prevent the inadvertent movement of the touching pad after the tail portion of the pad is inserted into the opening of the pincer. For pincers with a hole opening, the tail portion of the pad is preferably tapered, it has a front end matching the size and shape of the hole bored on the moving end of the pincers and a rear end slightly larger than the front end and the stem to allow the tail portion to act as a one way plug and prevent the pad from dislodging after insertion into the hole. The tail portion may also be shaped rectangularly especially if the opening is a track rather than a hole. The rectangular tail portion is inserted into the track and the head portion positioned on the upper or top band after insertion. The touching pad described can have the pad installed directly into the openings on the pincers by inserting or squeezing the tail portion of the pad into the openings to situate and expose the head portion of the pad on or above the outside surface of the pincers. The pad holders suitable for these pads with a tail portion are the ones with the lower band bordering an open space or the L-shaped claw to accommodate the tail portion. If the opening bored on the pincer is a hole, the touching pad remains stationary in one location. If the opening is a track, the touching pad is movable. The location of the touching pad can be varied by sliding the touching pad along the length of the track. A touching pad can be installed on tweezers without a hole or track bored on the pincers such as the present tweezers on the market. In this case, the pad used does not have a stem and tail portion and has to be supported by a pad holder. These pads can use all the pad holders described above. A suitable pad has a planar body preferably with an ergonomically shaped top surface to accommodate the fingers, a bottom surface and laterally protruding lips along its periphery extending farther than the inside peripheral contour of the upper or top band of the pad holder. The protruding lip lodges against the bottom surface of the upper or top band. The planar body of the pad also fills the open space bordered by the upper or top band of the touching pad holder. Because the pad here does not physically connect with the pincers unlike the pad with a tail inserting into the openings of the pincers, the touching pad holder supporting the pad may be glued to the pincers for reinforcement or the bottom surface of the pads directly touching the pincers may be roughened or provided with bumps, protrusions and the like, all meant to provide frictional resistance from movement of the touching pad. A vital feature of this invention is the touching pad covering or protruding from the top surface of either the pincers or the upper or top band of the touching pad holder to prevent the fingers from pressing into a hard surface.

A method for assembling a touching pad having a pad holder on a tweezers with an opening bored on each pincer at a location where the touching pad is desired, comprises inserting the pad holder into each moving end of the pincer through a slit of the pad holder, the pad holder having an upper or top band bordering an open space and means for keeping a pad engaged with the moving end of the pincers, the means joined to the upper or top band at each lateral end with a strip having a height corresponding to the thickness of the pincers; advancing the pad holder to a location where the touching pad is desired; and, installing the pad having a head portion, a tail portion and a stem portion connecting the head portion with the tail portion, into the touching pad holder by entering the tail portion through the upper or top band of the touching pad holder and inserting the tail portion into the opening exposed at a central area of the open space bordered by the upper or top band of the touching pad holder thereby situating the touching pad holder on the pincer and exposing the head portion of the pad on or above the upper or top band of the touching pad holder.

For tweezers without a hole bored on the pincers, the method of assembling a touching pad with a pad holder on a tweezers, comprises slipping a pad having a planar body with an ergonomically shaped top surface, a bottom surface and laterally protruding lip along its periphery into a touching pad holder having an upper or top band bordering an open space and means for keeping the pad engaged with the moving end of the pincers, the top surface of the pad entering from under the upper or top band of the touching pad holder through the open space and exposing the top surface of the pad on or above the upper or top band of the touching pad holder; and, inserting the touching pad holder having the pad into each pincer of the tweezers through the slit or L-shaped claw of the pad holder until the touching pad fits snugly on the pincers. The touching pad holder may be glued to the pincers for reinforcement if desired or the bottom surface of the pad may be roughened to provide frictional resistance to inadvertent movement.

DETAILED DESCRIPTION OF THE INVENTION

The invention relates to a tweezers 1 with a finger touching pad 100 to provide comfort to the fingers, usually the forefinger and thumb as they press into the pincers or the moving arm of the device. FIGS. 1–6 show the perspective view of the padded tweezers having the touching pad 100. It is simple in construction and is made up of the body 2, the pad 4 and a touching pad holder 3, if desired. The body 2 of the tweezers has a distal end 5 and a proximal end 6. The tweezers has two pincers or arms 7 fused together on the distal end 5 to form a stationary end 8 and a moving end 9 at the proximal end 6.

The invention herein proposes methods of padding a tweezers. One method requires boring an opening 10 which can be a hole 10a or a track 10b on each moving end 9 of the tweezers where the finger touching pad 100 will be positioned and installed. The other method does not need an opening bored on the pincers 7 of the tweezers to cater to the conventional tweezers. However, all these methods result in basically the same padded tweezers shown in FIGS. 1–6.

Figure 2:
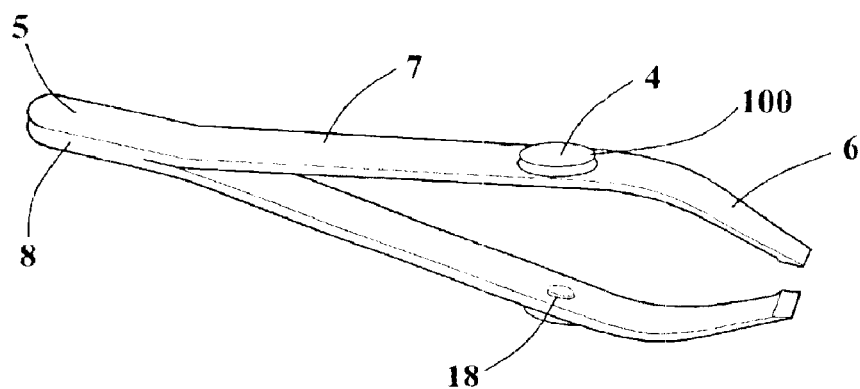
FIG. 2 is a perspective view of a padded tweezers with a pad on each pincer inserted into an opening on the pincer.
Figure 3:
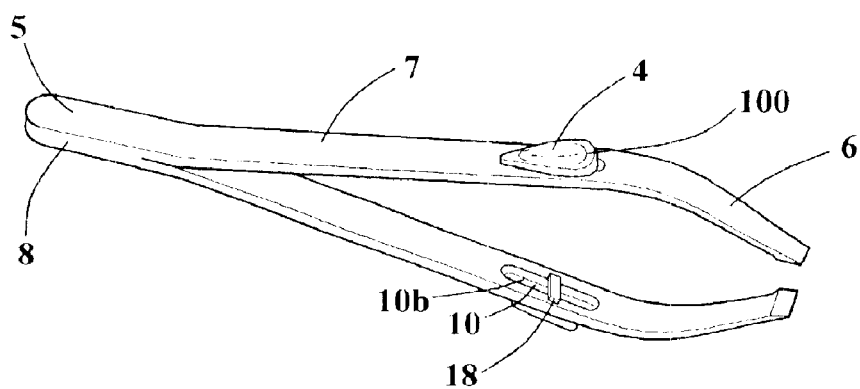
FIG. 3 is a perspective view of a padded tweezers with a pad on each pincer inserted into a track opening on the pincer.
Figure 4:
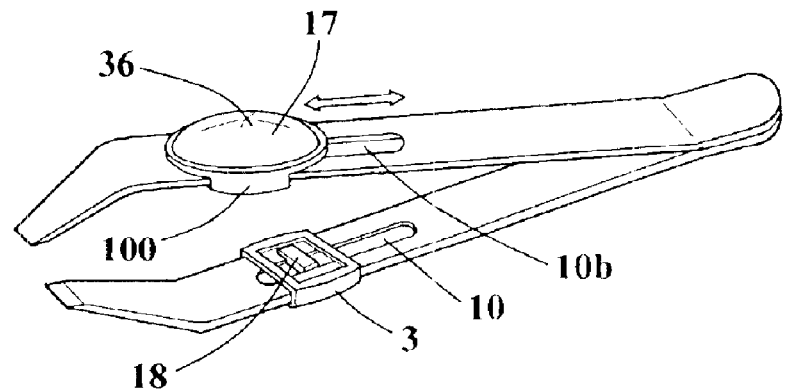
FIG. 4 is a perspective view of a padded tweezers having a pad supported by a pad holder on each pincer inserted into a track opening on the pincer.
Figure 4A:
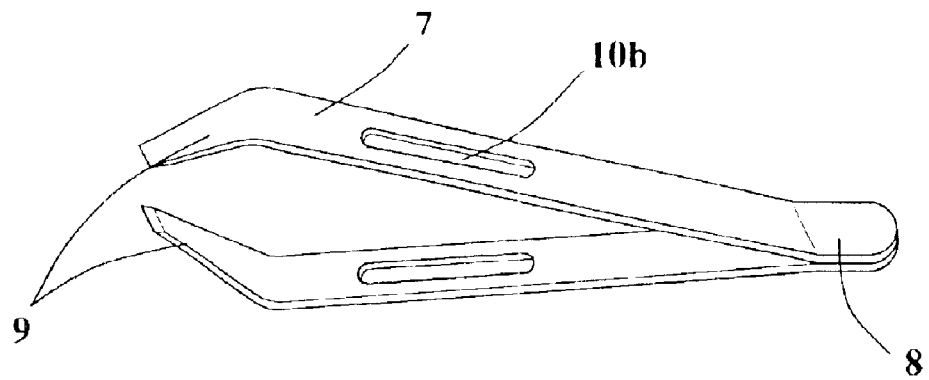
FIG. 4A is a perspective view of a tweezers having a track opening bored on the pincers.
Figure 5:
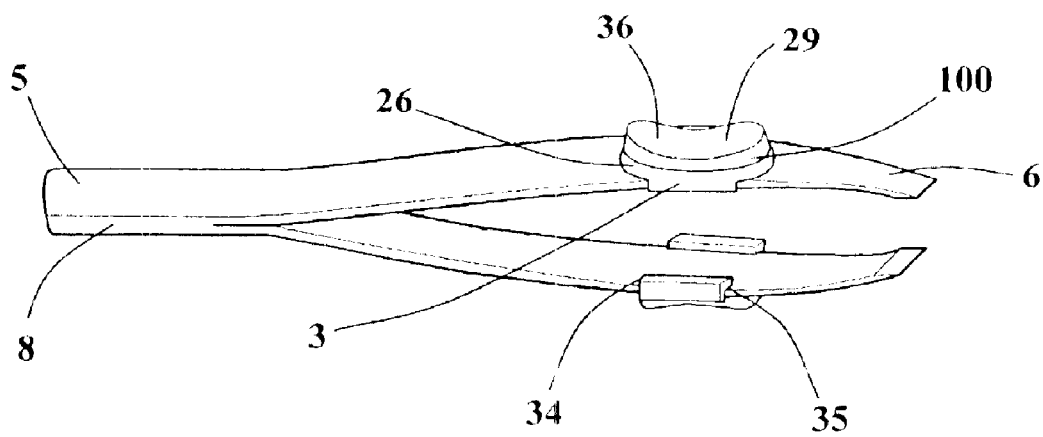
FIG. 5 is a perspective view of a padded tweezers having a pad supported by a pad holder with L-shaped claws.
Figure 6:
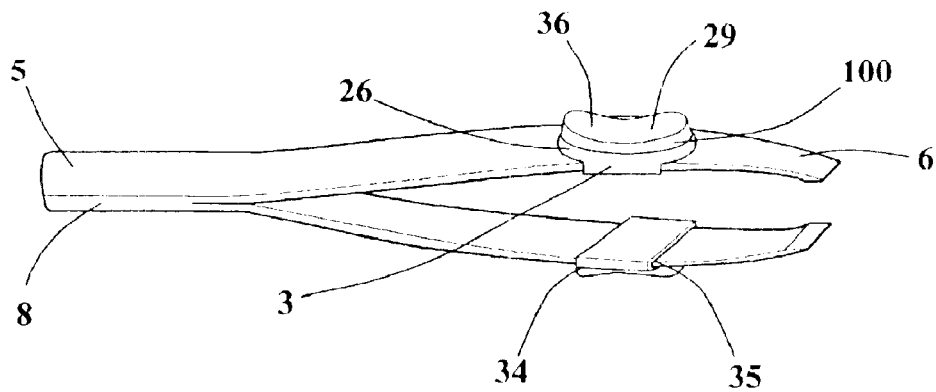
FIG. 6 is a perspective view of a padded tweezers having a pad supported by a pad holder with a solid lower band.
Figure 7:
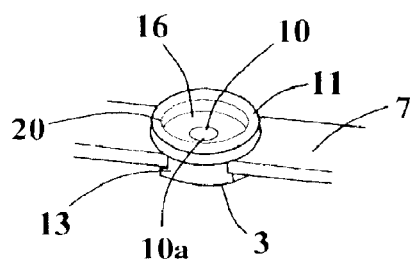
FIG. 7 shows the tweezers with a touching pad holder positioned relative to an opening bored at the moving end of the body.
Figure 8:
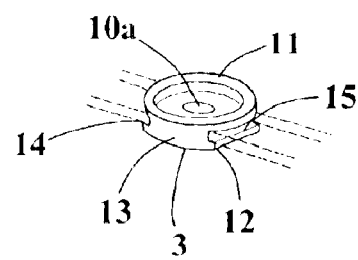
FIG. 8 is a perspective view of the touching pad holder having an upper band and a lower band, each bordering an open space.
Figure 9:
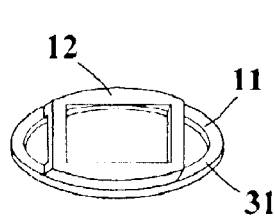
FIG. 9 is a back view of the pad holder of FIG. 8 having a front and back slit of the same widths.
Figure 9A:
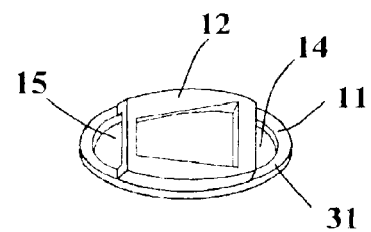
FIG. 9A is a back view of the pad holder of FIG. 8 having a front and back slit of different widths.
Figure 10:
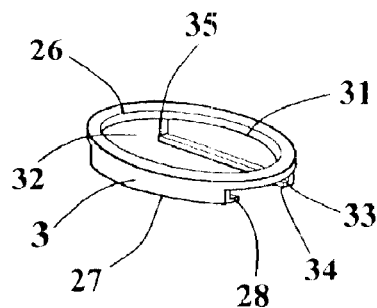
FIG. 10 is a perspective view of the touching pad holder having an L-shaped claw.

On the method requiring an opening 10 on the moving end of the tweezers, a touching pad 100 having a touching pad holder 3 is installed on the tweezers by slipping the pad holder into each pincer or arm 7 of the tweezers 1 as shown in FIGS. 1–4. The touching pad holders 3 suitable for this method are shown in FIGS. 1, 4 and 5. The pad holder shown in FIGS. 7, 8, 9, 9A, 14A and 14B has an upper band 11 preferably oval or rounded in shape and a lower band 12 joined at each lateral end with a strip 13 having a height corresponding to the thickness of the pincers 7. The outside lateral surface of the strip usually correspond to the shape of the lateral end of the upper band 11. If the upper band is oval or rounded, the outside lateral surface of the strip is curved accordingly. The inside lateral surface of the strip conforms to the outside lateral contour of the pincer. The lower band 12 need not be oval in shape but it can be any geometric shape so long as the upper 11 and lower 12 band joined and bordered by the lateral strips 13 forms a slit through which a moving arm or pincer 7 can be introduced. The width of the slits may differ in size if for example, the width of the pincers 7 tapers towards the proximal tip as shown in FIG. 9A, contrasted from FIG. 9. The difference in width may not be as pronounced as illustrated. In a tapering pincer, the front slit 14 through which the pincer 7 enters is wider than the back slit 15 of the touching pad holder 3. It is constructed this way so that the touching pad holder 3 stops advancing towards the stationary end 8 of the tweezers when the width and height of the front slit 14 matches the width and height of the pincer. At this position, the narrower width and height of the back slit 15 should also match the narrower width and height of the pincer to allow the touching pad holder to snugly fit or engage with the pincer at the location where the touching pad is desired. The width and height of the front and back slits of the pincers are the same if the widths and height of the pincers on which the touching pad 100 is placed do not vary. The height of the pincer is the same as the thickness of the pincer. For the tweezers having a hole on the moving end of the pincers, the touching pad holder 3 should stop advancing when the hole 10a is at a central area of the open space bordered by the upper band 11 as shown in FIGS. 7 and 8. For pincers with a track opening as shown in FIG. 4A, the width and thickness of the pincers do not usually vary through the length of the track. In this case, the position of the touching pad 100 can be varied by sliding the touching pad at positions along the length of the track opening as shown in FIGS. 3 and 4. For the pad holder 3 having an L-shaped claw 28 shown in FIGS. 5 and 10, the installation is the same as above but instead of the pincer entering a front and back slit, the pincer enters a front end claw 34 and a back end claw 35. The relationship of the widths of the L-shaped claws facing each other and the length of the overhang, which is the same as the height of the slit, to the width and height of the pincer is the same as described above for the pad holder having a lower band. This pad holder 3 has a top band 26 like the pad holder illustrated above. The top band 26 is constructed the same as the upper band 11 but is given a different numbering only to differentiate the band associated with the L-shaped claw means from that of the lower band means for engaging the pad. Reference to the upper band also refer to the top band. The lateral sides of the touching pad holder extends downward to form an overhang 27 as shown in FIGS. 5 and 10. The tip of the two overhang extends inward to form the L-shaped claw 28 where the pincer of the tweezers rests once the touching pad holder 3 is inserted into each pincer of the tweezers 1. Comparing the touching pad holders shown in FIGS. 7 and 8 with the touching pad holders shown in FIGS. 5 and 10, it is apparent that the L-shaped claw 28 of the pad holder is merely the lower band of the touching pad holder shown in FIG. 8 and 14A with a central portion cut out.

After lodging the chosen touching pad holders 3 on the respective pincers 7, a pad 4 that is soft and resilient complimenting the characteristics of the human finger, is introduced into the opening 10 to fill the open space 16 bordered by the upper band 11 or the open space 32 bordered by the top band 26 as shown in FIGS. 1, 4 and 5. FIGS. 11A and 11B show the front view of the pad 4 as seen facing the proximal end 6. The pad shown in FIG. 11A is catered more to the pincer with a hole opening 10a while the one shown in FIG. 11B is catered to the pincer with a track opening 10b. The pad has a head 17 portion and a tail 18 portion. The peripheral contour 19 of the head portion 17 matches the inside peripheral contour 20 of the upper band 11 or the open space 32 bordered by the top band 26 of the touching pad holder 3. The head 17 portion is connected to the tail 18 portion by a stem 21 matching the size and shape of the opening 10 such as the hole 10a or the width of the track 10b. The height of the stem matches the thickness of the pincer 7. The tail 18 portion of the pad 4 shown in FIG. 11A preferably has tapering side walls 22 to facilitate the introduction of the pad 4 into the hole 10a. The surface area of the front end 23 of the tail portion matches the size and shape of the opening but the rear end 24 of the tail 18 portion is slightly larger than the front end 23 and the stem 21 so that the tail 18 acts as a one way plug to prevent the pad 4 from dislodging after it has been introduced into the opening. While the opening herein is shown as circular in shape, any geometric shape can be used so long as the tail and stem of the pad matches the size and shape of the opening. Also, while the head portion of the pad herein is shown mostly as oval in shape, other geometric shapes can also be used so long as its contour matches the contour of the upper band 11 or top band 26 of the touching pad holder if a pad holder is used. The top surface 36 of the head is ergonomically shaped to accommodate the fingers. The touching pad 100 installed on the pincers having a hole opening is stationary. When the pincer has a track opening instead of a hole opening as shown in FIGS. 4 and 4A, the pad 4 shown in FIG. 11B is preferred. Here, the tail 18 is rectangularly shaped and runs across the head 17 as shown in FIG. 4. To install this, the rectangularly shaped tail is inserted along the same axis as the track and after insertion, the pad 4 is turned approximately 90 degrees to allow the head 17 to match and cover the inside peripheral contour 20 of the upper band 11 or the open space 32 bordered by the top band 26 of the touching pad holder 3. Further, while it is demonstrated here that a touching pad holder 3 supports the pad 4 installed into the pincers of the tweezers, it is also possible to install the touching pad 100 consisting of the pad 4 alone directly into the pincers 7 by inserting or squeezing the tail 18 of the pad into the opening 10 absent any touching pad holder as shown in FIGS. 2 and 3.

For tweezers without an opening on the pincers such as those currently sold, the pad for this type of holder does not have a stem portion. Rather, the pad 29 has a planar body with an ergonomically shaped top surface 36, a bottom surface 25 and laterally protruding lip 30 along its periphery as shown in FIG. 12. To install the pad into this holder 3, the pad 29 is first slipped into the slits or L-shaped claw and inserted from the bottom and into a touching pad holder 3. The lip 30 of the pad extends farther than the inside peripheral contour of the upper or top band, thereby lodging against the bottom surface 31 of the upper band 11 or the top band 26. The pad 29 fills the open space 16 or 32 bordered by the upper band 11 or the top band 26, respectively. Once the pad 29 is engaged with the pad holder 3, the pad holder is inserted into each pincer through the slit or the L-shaped claw 28 opening at each end 33 of the touching pad holder 3 or through the front 14 and back slit 15 of the pad holder with a lower band. The pincers keep the pad from getting out of the touching pad holder because the inserted pincers situate underneath the bottom surface 25 of the pad as shown in FIG. 5. The bottom surface 25 of the pad may be roughened in texture or provided with bumps and protrusions, herein collectively referred to as roughened bottom surface. FIG. 13 shows the pad 29 with the bottom surface 25 provided with bumps 37. These roughened bottom surface reinforces the attachment of the touching pad 100 to the pincers due to the frictional resistance to movement provided by these type of surfaces. The touching pad 100 may also be glued to the pincer for reinforcement. Also, for this type of pad, a pad holder with a solid lower band midpoint of the upper or top band extending across the strip joining the upper or top band can be used. The solid band 38 may be wide or narrow as shown in FIGS. 14A and 14B. As in the other pad holders, the relationship of the dimensions of the slit to the dimensions of the pincers when the pad holder is inserted to the pincers is as described above. This type of pad holder, however, can not be used with pad 4 because the tail portion of the pad will get into the way of the solid band.

All the touching pad 100 having pad 29 on the pad holders 3 above, if not glued to the pincers, can be moved to a desired location along the moving end of the pincers. The roughened bottom surface 25 on the pad help keeps the touching pad 100 in place while the tweezers are in use. With the roughened bottom surface, inadvertent movement of the touching pad is better avoided as long as the width and thickness of the pincers are not materially different from the dimensions of the slits and the L-shaped claw openings. The pad 29 for the pad holder with a solid lower band 38 preferably has a cut out portion 39 on the bottom surface as shown in FIG. 15 adjacent to the strip joining the solid lower band to accommodate the strip and ensure that the pad inserts snugly into the upper or top band 11 or the top band 26 of the pad holder.

Regardless of what method is used to pad the tweezers, the pad 4 or 29 covers the open space or protrudes from the top surface of the top band 11 or 26 as shown in FIGS. 1 4, 5 and 6 or the pincers 7 as shown in FIGS. 2 and 3 so that a user will not feel any hard surface pressing on the fingers. The pad holders are made of plastic or light metal. Examples of materials that can be used to make the pad are rubber based material, silicone, and gel. For the gel, the top surface 36 of the pad need not be shaped to ergonomically accommodate the fingers because the gel will naturally acquire the shape of the fingers. However, for the non-gel but soft and resilient material such as latex and silicone, the top surface 36 may be concaved, convexed, or sloped in one end. The shape of the top surface is at the discretion of the user. For surgical usage, the pad 4 or 29 are preferably made of materials that can be sterilized.

The above invention is usually used by the thumb and forefingers pressing on the touching pad when the fingers pinch on an object for transfer, removal, placement or plucking.

The touching pads described above may be replaced when it gets worn out with usage or gets a dirty appearance by simply detaching and replacing the pad from the opening on the pincers or by slipping the touching pad out of the pincers and replacing the pad on the pad holder.

While the embodiment of the present invention has been described, it should be understood that various changes, modifications and adaptations may be made therein without departing from the spirit of the invention and the scope of the appended claims. Those skilled in the art will recognize that other and further variations of the features presented herein are possible. The scope of the present invention should be determined by the teachings disclosed herein, the appended claims and their legal equivalents.

I claim:

1. A tweezers with touching pads at a location on each pincer to improve the grip and prevent formation of callouses and corns, comprising:
   a body having two pincers with a stationary end and a moving end; and,
   a touching pad holder supporting a soft and resilient pad for each pincer, the touching pad holder comprising an upper or top band having a peripheral contour bordering an open space and a means for keeping the pad engaged with the moving end of the pincers, the means joined at each lateral end of the upper or top band with a strip having a height corresponding to the thickness of the pincer.

2. The tweezers of claim 1 wherein the means for keeping the pad engaged with the moving end of the pincers is a lower band having a peripheral contour bordering an open space, the lower band joined by the strip to form a slit.

3. The tweezers of claim 1 wherein the means for keeping the pad engaged with the moving end of the pincers is a solid lower band extending across the strip joining the upper or top band, the solid lower band and the strip forming a slit.

4. The tweezers of claim 1 wherein the means for keeping the pad engaged with the moving end of the pincers is an L-shaped claw.

5. The tweezers of claim 1 wherein the strip has an outside lateral surface corresponding to the shape of the upper or top band and an inside lateral surface conforming to the outside lateral contour of the pincers.

6. The tweezers of claim 1 wherein the touching pad holder snugly fits at a location on the pincer where the touching pad is desired.

7. The tweezers of claim 1 wherein the pad fills an open space bordered by the upper or top band.

8. The tweezers of claim 1 wherein the pad has a head portion having a top surface matching an inside peripheral contour of the upper or top band of the touching pad holder, a tail portion and a stem connecting the head portion with the tail portion, the stem having a size and shape matching an opening on the pincers and a height matching the thickness of the pincers.

9. The tweezers of claim 8 wherein the tail portion of the pad has a front end matching the size and shape of the opening bored on a moving end of the pincers and a rear end slightly larger than the front end and the stem, the tail portion acting as a one way plug to prevent the touching pad from dislodging after insertion of the tail portion into the opening.

10. The tweezers of claim 8 wherein the tail portion of the pad is shaped rectangularly.

11. The tweezers of claim 1 wherein the pad has a planar body, a top surface to accommodate a finger, a bottom surface and laterally protruding lip along its periphery extending farther than the peripheral contour of the upper or top band thereby lodging against a bottom surface of the upper or top band, the pad filling the open space bordered by the upper or top band of the touching pad holder.

12. The tweezers of claim 11 wherein the bottom surface of the pad is roughened to provide frictional resistance to movement.

13. The tweezers of claim 1 wherein each pincer has a hole opening for keeping the touching pad stationary or a track opening for allowing the touching pad to slide along the length of the track.

14. The tweezers of claim 1 wherein the touching pad holder is glued to the pincers.

15. The tweezers of claim 1 wherein the pad protrudes from the top surface of the touching pad holder to prevent the fingers from pressing on the touching pad holder.

16. The tweezers of claim 1 wherein the pad has an ergonomically shaped top surface to provide comfort for the fingers.

17. A method for assembling a padded tweezers, comprising:

boring an opening on each pincer at a location where a touching pad is desired;

inserting into each moving end of the pincer a touching pad holder having an upper or top band bordering an open space and means for keeping the pad engaged with the moving end of the pincers joined at each lateral end of the upper or top band by a strip having a height corresponding to the thickness of the pincers, until the touching pad holder stops advancing at a point when the opening is exposed at a central area of the open space bordered by the upper or top band of the touching pad holder; and, installing a pad having a head portion, a tail portion and a stem portion connecting the head portion with the tail portion, into the touching pad holder by entering the tail portion through the open space bordered by the upper or top band of the touching pad holder and squeezing the tail portion into the opening exposed at the central area of the upper or top band of the touching pad holder thereby situating the touching pad holder on the pincer and exposing the head portion of the pad above the upper or top band of the touching pad holder.

18. A method for assembling a padded tweezers without a hole bored on the pincers, comprising:

installing a pad having a planar body with a top surface, a bottom surface and laterally protruding lip along its periphery into a touching pad holder having an upper or top band bordering an open space and means for keeping the pad engaged with the moving end of the pincers joined at each lateral end of the upper or top band by a strip having a height corresponding to the thickness of the pincers by slipping the top surface of the pad from under the upper or top band of the touching pad holder through the open space and protruding the top surface of the pad above the upper or top band of the touching pad holder; and, inserting the touching pad holder having the pad into each pincer of the tweezers until the touching pad fit snugly on the pincers.

19. The method of claim 18 further comprising the step of gluing the touching pad holder having the pad into the pincers.

20. A tweezers with finger touching pads on each pincer to improve the grip and prevent formation of callouses and corns, comprising:

a body having two pincers with a stationary end and a moving end, the two pincers having an opening bored at a location on the moving end where a touching pad is desired; and, a soft and resilient pad inserted into the opening of the two pincers, the pad having a head portion, a tail portion and a stem portion connecting the head portion with the tail portion, the stem having a size and shape matching the opening and a height matching the thickness of the pincer, the head portion locating above the outside surface of the pincers after insertion.

21. A method for assembling a tweezers having a soft and resilient touching pad inserted into a moving end of each pincers, comprising:

boring an opening on each pincer at a location where a touching pad is desired; and, installing a pad having a head portion, a tail portion and a stem portion connecting the head portion with the tail portion into an outside surface of each pincer by squeezing the tail portion into the opening on the pincer to situate and expose the head portion of the pad above the outside surface of the pincers, the stem portion having a height the same as the thickness of the pincers thereby preventing movement of the touching pad.

* * * * *